| United States Patent [19] | [11] Patent Number: 4,610,960 |
| Mosher | [45] Date of Patent: Sep. 9, 1986 |

[54] MONOCLONAL ANTIBODY TO THROMBOSPONDIN AND METHOD FOR ASSAYING FOR AND ISOLATING THROMBOSPONDIN

[75] Inventor: Deane F. Mosher, Madison, Wis.

[73] Assignee: Wisconsin Alumni Research Foundation, Madison, Wis.

[21] Appl. No.: 565,024

[22] Filed: Dec. 21, 1983

[51] Int. Cl.$^4$ .................. G01N 33/53; C12P 21/00; A61K 39/395; C12N 5/00
[52] U.S. Cl. .................................. 435/7; 435/68; 435/172.2; 435/240; 435/948; 436/548; 935/103; 935/110; 530/387
[58] Field of Search .................. 435/7, 68, 240, 172.2, 435/948; 436/548, 513; 935/95, 103, 110; 260/112 R, 112 B; 424/85

[56] References Cited

U.S. PATENT DOCUMENTS 4,376,110  3/1983  David et al. .................. 436/540

OTHER PUBLICATIONS

Jaffe et al, Proc. Nat'l. Acad. Sci. USA, 80:998–1002 (Feb. 1983).
Jaffe et al, Nature, 295:246–248 (Jan. 21, 1982).
McClaren, J. Clin. Path., 36:197–199 (Feb. 1983).
Sage et al, Biochem., 22:2148–2155 (Apr. 1983).
Hagen et al, Biochem. Biophys. Acta, 732:600–606 (1983).

*Primary Examiner*—Esther M. Kepplinger
*Attorney, Agent, or Firm*—David J. Houser

[57] ABSTRACT

A monoclonal antibody produced by a hybridoma formed by the fusion of cells from a mouse myeloma line and spleen cells from a mouse previously immunized with thrombospondin. The monoclonal antibody reacts with human, bovine, and canine thrombospondin but not with the thrombospondin present in rabbit serum. The monoclonal antibody is capable of being used to identify human, bovine, and canine thrombospondin in ELISAs and by means of immunohistological techniques and also can be used to isolate such thrombospondin by when employed in immunoisolation techniques.

16 Claims, No Drawings

MONOCLONAL ANTIBODY TO THROMBOSPONDIN AND METHOD FOR ASSAYING FOR AND ISOLATING THROMBOSPONDIN

This invention was made with Government support under NIH Grants Nos. 5R01 HL 24885-02, 5R01 HL 24885-03, 2R01 HL 21644-04, 5R01 HL 21644-05 and 5R01 HL 21644-06 awarded by the Department of Health and Human Services. The Government has certain rights in this invention.

TECHNICAL FIELD

This invention relates generally to a hybrid cell line adapted to produce monoclonal antibodies, and, more specifically, to such a cell line producing a monoclonal antibody to thrombospondin.

BACKGROUND OF THE ART

The art is generally cognizant of the basic technique of fusing mouse myeloma cells to spleen cells from immunized mice to obtain a culturable, continuous cell line capable of producing homogeneous or "monoclonal" antibodies. See, for example, Kohler and Milstein, Nature 256, 495–497 (1975). Attempts to apply this general knowledge are often frustrated by particular problems and difficulties encountered with regard to particular antigens. Furthermore, the complexity of such antigens, the almost inevitable inclusion in inocula of other, accidentally associated antigenic material, and the existence of various incidental immunities in the mice whose spleen cells are used prevent any assurance that the monoclonal antibody eventually produced will in fact be to the target antigen.

In biological systems, complex antigens commonly change as they move from one context to another within an organism. A monoclonal antibody to the antigen may recognize it only in one form. Likewise, when the antigen for which a monoclonal antibody is desired appears in corresponding forms in various species, it is not uncommon that the antigen varies slightly from species to species. Consequently, there is no assurance that any particular cross species specificity will be obtained or that even within a given species an antigen will be recognized in any particular biological context.

In the production of monoclonal antibodies and the hybridomas making them, a convenient experimental animal, such as a mouse, is exposed to the antigen against which an antibody is desired. Typically, some of the antigen is injected into the animal, and its immune system is allowed to respond to it. This process may be repeated until the animal's immune system is presumed to be producing antibodies to the antigen, as well as such other antibodies as the animal may be producing without regard to the injections of the antigen. The animal is then killed, and antibody-producing cells from it are isolated. Typically spleen cells from the animal are employed.

A large number of such spleen cells are then fused with myeloma cells of the same species to obtain hybrid cells that will reproduce without the self-limiting growth characteristics of most non-tumor cells. The fused cells are then cultured as cell lines of genetically identical, antibody-producing cells. However, there is no assurance that the antibody produced by any particular cell line is an antibody to the original antigen or that the antibody will be specific to the antigen. In order to select from among the many hybridoma cell lines thus created for a particular cell line that produces a desired antibody, it is necessary to screen the cell lines. This is done by testing the antibody produced by each cell line against the original antigen or a purified form thereof. The cell lines that are found by this means to produce the desired antibody are then preserved, and the remainder are discarded.

It should be emphasized again that the unpredictable nature of hybrid cell preparation generally does not allow one to extrapolate from one antigen or cell system to another in order to predict precise outcomes of the application of conventional hybridization techniques. This unpredictability is further increased as the antigen is more complex and as an antibody is sought capable of recognizing the antigen in more than one species or in more than one form or context within a biological system.

Thrombospondin is the major glycoprotein released from alpha granules of thrombin-stimulated blood platelets. In addition, thrombospondin is synthesized by growing cells. See Mosher, Doyle, and Jaffe, "Synthesis and Secretion of Thrombospondin by Cultured Human Endothelial Cells," J. Cell Biol. 93, 343–348 (1982); Raugi et al., "Thrombospondin: Synthesis and Secretion by Cells in Culture," J. Cell Biol. 95, 351–354 (1982).

Blood platelet alpha granules are membrane-enclosed sacs contained within the body of the platelet. Each platelet has a number of alpha granules. Alpha granules contain a variety of proteins including thrombospondin, platelet factor 4, and beta thromboglobulin. In addition, other proteins are contained within alpha granules that are related to or identical with certain plasma proteins that take part in blood clotting, such as fibrinogen and accelerin (blood coagulation factor V). When platelets are stimulated by thrombin, for example as part of the body's response to trauma to a blood vessel, the alpha granules discharge their contents into the blood, the proteins contained therein participating further in various ways in the aggregation of platelets and related processes.

In various contexts, it is useful to be able to determine routinely the presence and the quantity of thrombospondin in a sample of material. For example, fetal calf serum is a commercially available material extensively used in cell culturing and other experimental and commercial operations. As is the case with any material used in sensitive procedures, it is important to be able accurately to characterize fetal calf serum. For example, it is important to determine the amount of particular materials that are present in fetal calf serum in varying quantities, depending upon the source of the serum and the conditions of preparation. The proteins released from platelet alpha granules are an example of materials that are present in varying quantities in fetal calf serum. Currently tests for platelet factor 4 and beta thromboglobulin are utilized not just to determine the presence of those materials but as an indication of recent platelet activation in human patients, since both of those materials form part of the contents of alpha granules which are released during platelet activation. However, tests for these materials in blood plasma have not proved reliably sensitive and specific for alpha granule release. It is speculated that these two materials are rapidly cleared from the circulation once released from platelets, making it impossible to precisely relate their concentrations to the likely concentrations of other materials released with them from alpha granules. The ability to test quantitatively for the presence of thrombospondin would provide an additional and probably superior means to test for alpha granule release.

A reliable, specific, and quantitative test for thrombospondin would be an important research tool with various applications. For example, there are indications that elevated levels of thrombospondin in blood plasma may be characteristic of disseminated intravascular coagulation associated with septicemia, thrombotic thrombocytopemia purpura, cancers, and neoplasms. Quantitative assays for thrombospondin would have application in studies of these conditions and in the examination of lysed platelets and of joint fluids from people with various types of arthritic conditions and other joint diseases or abnormalities. A monoclonal antibody specific to thrombospondin would further allow the specific measurement of thrombospondin in a variety of biological fluids and cell and tissue extracts, for example by enzyme-linked immuno-sorbent assays, (hereinafter "ELISAs") and other immunoassays. In other contexts, such an antibody would allow locating thrombospondin in a tissue section by immunofluorescence and other immunohistological techniques. In vivo the presence of thrombospondin could be detected by nuclear scanning for a radiolabeled version of such an antibody.

It is possible to produce anti-thrombospondin antibodies by conventional innoculation of rabbits or other animals followed by the processing of serum later extracted from the innoculated animal. The attempted production of a monoclonal antibody to thrombospondin has not been reported.

SUMMARY OF THE INVENTION

The present invention is summarized in that a monoclonal antibody of class IgG is produced by a hybridoma formed by the fusion of cells from a mouse myeloma line and spleen cells from a mouse previously immunized with thrombospondin, which antibody reacts with human, bovine, and canine thrombospondin and not the thrombospondin present in rabbit serum. The invention is further summarized to include the hybridoma ATCC HB8432.

A primary object of the invention is to provide a monoclonal antibody to human thrombospondin.

A second object of the invention is to provide such an antibody capable of specific recognition of thrombospondin both when released into blood plasma, serum, and other biological fluids and when retained in non-fluid tissue when synthesized by growing cells and otherwise.

A further object of the invention is to provide such an antibody capable of recognizing bovine thrombospondin in fetal calf serum.

Yet another object of the invention is to provide such an antibody capable of recognizing trypsinized thrombospondin.

A further object of the invention is to provide such an antibody that can be used in ELISAs and other immuno assays as well as in various immunohistological techniques for the measurement and detection of thrombospondin, and likewise for nuclear scanning for radiolabeled antibody and the like for in vivo detection of thrombospondin.

Other objects and advantages of the invention will be apparent from the following detailed description setting forth the preferred embodiment of the invention.

DETAILED DESCRIPTION OF THE PREFERRED EMBODIMENT

In general overview, a BALB/c mouse was immunized with purified human platelet thrombospondin. Spleen cells from the mouse so immunized were fused with mouse myeloma cells, fusion being effected with treatment in polyethylene glycol in accord with known methods. Resulting hybridomas were cultured and then selected for antibody activity. Cells producing anti-human platelet thrombospondin were detected by means of an ELISA, in the manner well known in the art. A clone that produces an IgG having the mobility of a gamma globulin was selected for antibody production in mice. Antibody was purified from ascites fluid in conventional ways. The clone cell line so created and selected was perpetuated by conventional cell culturing techniques.

The hybridoma so produced has been deposited at the American Type Culture Collection and has been assigned the designation: HB8432. This particular hybridoma and antibodies produced thereby are the hybridoma and monoclonal antibodies referred to below, unless otherwise stated. A detailed description of the making of the hybridoma is included below as an example.

The antibody was tested for specificity by competitive ELISAs and by immunoblotting of platelet extracts, plasma, serum, and both unaltered and trypsinized purified thrombospondin. By these means it was determined that the antibody does not react with any serum or platelet protein except thrombospondin. The antibody recognizes bovine and canine thrombospondin. The antibody does not recognize thrombospondin present in rabbit or mouse serum. Trypsin digests thrombospondin to leave a disulfide-bonded core. The antibody was found to be specific to the disulfide-bonded core remaining after trypsin digestion of human thrombospondin. Examples illustrative of the tests for specificity referred to are set forth in the examples below.

Competitive ELISAs are a conventional method for assaying for the presence of an antigen in a sample of test material. The competitive ELISA of the invention is adapted to quantitatively assay for the presence of thrombospondin in a sample of test material and includes the following steps. First, known thrombospondin is bound to a suitable adsorbtor substrate. Preferably a plastic culture plate is used, such as the 96 well polystyrene culture plates sold by Costar, Cambridge, Mass. as Model No. 3596. A solution known to contain thrombospondin is placed in each of the wells and allowed to remain under conditions such that thrombospondin from the solution is adsorbed to the surface of the wells. The solution is then washed away, leaving the thrombospondin bound to the adsorbtive walls of the wells, which shall be referred to as "adsorbtor substrate units." With thrombospondin adsorbed to them, they shall be referred to as "thrombospondin charged substrate units."

Next, a known quantity of the test material is exposed to a known quantity of the monoclonal antibody referred to above. Preferably a series of dilutions of the test material are made, which can be conveniently done in a second 96 well culture plate. Samples of each dilution are then exposed to a known quantity of monoclonal antibody. The monoclonal antibody binds with the thrombospondin present in the test material to produce what will be referred to as a "reacted unknown sample." Enough monoclonal antibody is added so that, at some point in the series of dilutions of test material, antibody remains unbound to thrombospondin after a maximal amount of the binding sites on the thrombospondin present have been occupied by antibody.

A standard preparation of thrombospondin having a known concentration of thrombospondin is prepared, and preferably a series of dilutions are also made of the standard preparation. Selected quantities of the standard preparation thus having a known amount of thrombospondin are exposed to a known quantity of the monoclonal antibody so as to cause the antibody to bind to the thrombospondin to create a reacted standard sample. Preferably a series of such reacted standard samples are prepared from the various dilutions of the standard preparation of thrombospondin referred to above. As with the test material dilutions, at some point the amount of antibody is sufficient to occupy maximally the binding sites on the thrombospondin with an excess of antibody remaining in the reacted standard sample.

The reacted unknown samples are then each exposed to a thrombospondin charged substrate unit. Any as yet unreacted monoclonal antibody contained in the reacted unknown sample quantitatively binds to the thrombospondin adsorbed to the surface of the thrombospondin charged substrate units until a maximal amount of the binding sites thereon are occupied. Similarly, the reacted standard samples are exposed to thrombospondin charged substrate units to quantitatively react any yet unreacted antibody contained in the reacted standard samples with the bound thrombospondin thereon.

All monoclonal antibody not reacted with the bound thrombospondin on the thrombospondin charged substrate units then is removed. If the reacted unknown sample or reacted standard sample exposed to a particular charged substrate unit had no monoclonal antibody that had not been bound to the thrombospondin present in the test material or standard preparation of thrombospondin, no monoclonal antibody will remain on the thrombospondin charged substrate unit. If the amount of monoclonal antibody added to produce the reacted unknown or standard sample was so great that sufficient unreacted monoclonal remains to occupy maximally the binding sites on the thrombospondin adsorbed to the charged substrate units, the assay will be unable to distinquish between reacted samples containing just enough monoclonal antibody available to so bind maximally the binding sites and other samples having even more monoclonal antibody. However, for reacted unknown and standard samples falling between these extremes, monoclonal antibody not bound to thrombospondin in the test material or standard preparation will remain bound to the thrombospondin adsorbed to the surface of the charged substrate units. It will be apparent that as the thrombospondin concentration in the test material or standard preparation is lower, the amount of monoclonal antibody available to bind to the charged substrate units is greater. Thus, as increasingly dilute concentrations of thrombospondin are subjected to the steps disclosed, and monoclonal antibody not reacted with the bound thrombospondin on the thrombospondin charged substrate units is removed, for example by washing, the charged substrate units will be found to hold at first as little as no monoclonal antibody, then increasing amounts and finally an unvarying maximum amount as the binding sites on the charged substrate units are flooded with antibody.

The thrombospondin charged substrate units are then comparatively and quantitatively assayed for the presence of monoclonal antibody. Preferably this is done by exposing each thrombospondin charged substrate unit and the monoclonal antibody reacted therewith to a marker-coupled anti-mouse antibody to allow the marker-coupled antibody to bind to any monoclonal antibody present. Any unbound marker-coupled antibody is then removed, and the amount of marker remaining on the thrombospondin charged substrate units is measured. The marker may be an enzyme measured by its effect on a selected reagent, a fluorescent material, a radioactive material, or any other of the markers familiar to one skilled in the art. It will be apparent that the monoclonal antibody itself may be combined directly with a marker, whereupon the step of reacting a marker-coupled anti-mouse antibody may be omitted.

The monoclonal antibody may also be used in other conventional ELISAs. For example, a sample of test material may be bound to an adsorbtor substrate and then exposed to the monoclonal antibody disclosed above. The antibody binds to any thrombospondin present in the test material. Unbound portions of the monoclonal antibody are then removed. Next, an assay comparable to those discussed above is conducted for the presence of bound monoclonal antibody.

The monoclonal antibody of the invention may also be used in any of the generally known methods of using such antibodies in immunohistological techniques for examining a substantially cohesive, nonfluid test material, such as a cell or tissue sample. The test material is incubated with the monoclonal antibody to bind the antibody to thrombospondin present in the test material. The test material is then washed to remove the unbound portion of the monoclonal antibody. The antibody may then be treated in such a way as to make its presence visually apparent. Typically, the test material bearing monoclonal antibody bound to thrombospondin contained therein is incubated with a marker-labeled anti-mouse antibody comparable to those discussed above. The marker-labeled antibody binds to the monoclonal antibody. A marker is selected such that it may be made visually apparent. Fluorescent and enzyme markers typically are used. The test material is then microscopically observed under conditions adapted to render the marker visually perceivable.

Thrombospondin has a variety of experimental uses, including modification of the behavior of blood platelets. An efficient and specific technique for the purification of thrombospondin is provided by coupling the monoclonal antibody referred to above to conventional cyanogen-bromine activated agarose beads either processed in a batch or held within a conventional purification column. A solution containing the thrombospondin to be purified is then run through the column or exposed to the batch, the thrombospondin being bound to the beads by operation of the antibody. After suitable washing, the bound thrombospondin may be eluted from the beads in a purified solution from which other protein has thus been separated.

The examples below provide specific examples of the invention disclosed herein.

EXAMPLE 1

Preparation of the Cloned Cell Line

Preparation of Innoculum Antigen: Human platelet thrombospondin was prepared by the method described in full in Mosher, Doyle, & Jaffe, "Synthesis and Secretion of Thrombospondin by Cultured Human Endothelial Cells," *J. Cell Biol.* 93, 343–348 at 344 (1982). The purity of thrombospondin so obtained compared to the total protein content of the solution typically is approximately 97%, as estimated by densitometry. The concentration is typically 0.1 to 1 mg/ml.

Immunization of Mice: A BALB/cAu mouse was selected for immunization. The mouse was immunized by injection intraperitoneally with the innoculum antigen over a three-month period. Intraperitoneal injections of 50 μg of the innoculum antigen preparation referred to above were made 99 days apart. Four days following the second injection, the mouse was killed and its spleen removed for use.

Hybridization and Hybridoma Culture Methods: Spleen cells from the immunized mouse were fused with myeloma cells using the method of Kohler & Milstein, *Eur. J. Immunol.* 6, 511–519 (1976). The myeloma cells used were P3-Ns1-AG4 mouse myeloma cells. Fusion was effected with 40% polyethylene glycol ($M_r$ 1050). Fused cells were selected in a hypoxanthine/amethopterin/thymidine medium. They were then cultured further in hypoxanthine/thymidine medium. By this means, selection was made only for successfully fused cells.

Screening: Following the hybridization process disclosed above, the resulting hybrids were tested for anti-thrombospondin activity. They were so tested by means of conventional direct ELISAs. Cells producing anti-thrombospondin antibodies were subcloned twice by the method of Kohler & Milstein, *Nature* 256, 495–497 (1975). A clone was selected that produces an IgG having a mobility of a gamma globulin in conventional electrophoresis. This clone was perpetuated using conventional cell culturing techniques and is the cell line identified above as that given the designation HB8432 by the American Type Culture Collection (hereinafter ATCC HB8432.) Cloned cells were also used in the production of ascites by conventional injection of the cells into pristane-treated BALB/c mice. The antibody was purified from the resulting ascites fluid by conventional ammonium sulfate precipitation and chromatography on DEAE-cellulose.

EXAMPLE 2

Competitive ELISAs Using the Monoclonal Anti-Thrombospondin Disclosed Above

Supernatant of Thrombin-stimulated Washed Platelets: An ELISA was conducted of thrombospondin present in a supernatant collected from thrombin-stimulated, washed platelets. The supernatant was prepared in accord with the method set forth in Mosher, Doyle, & Jaffe, "Synthesis and Secretion of Thrombospondin by Cultured Human Endothelial Cells," *J. Cell Biol.* 93, 343–348 (1982). The materials contained in the supernatant and derived from the platelets shall be referred to herein as "platelet releasate." The supernatant was diluted within the limits 1:30 to 1:100 in 10 mM Tris-HCl 140 mM sodium chloride, pH 7.4 (Tris/NaCl), containing 0.1% bovine serum albumin. Platelet releasate is known to contain thrombospondin. Therefore the supernatant itself was used to prepare charged substrate units. To do so, 200 μl of the diluted supernatant solution, containing approximately 0.5 μg of thrombospondin, was placed in each well of a first 96 well polystyrene culture plate (Model No. 3596, sold by Costar, Cambridge, Mass.).

Thrombospondin standard was prepared in the same manner as was the thrombospondin that had been prepared as the innoculum antigen employed in the production of the monoclonal antibody disclosed above. The thrombospondin standard was stored at −70° C. at a concentration of 20 μg/ml in 0.5% bovine albumin. In some of the wells of a second 96 well culture plate, dilutions of the thrombospondin standard were made in 10 mM sodium phosphate/140 mM sodium chloride/1 mM EDTA, pH 7.4, containing 3% bovine albumin. In the remaining wells, like dilutions were made of the diluted supernatant of thrombin-stimulated washed platelets referred to above. The dilutions were so made that a total of 100 μl of fluid was placed in each well of the second culture plate. Then to each well an additional volume of 100 μl was added of Tris/NaCl solution containing 0.3% bovine albumin and 0.38 μg/ml of the mouse monoclonal anti-thrombospondin antibody referred to above. At least a portion of the monoclonal antibody reacted with any thrombospondin present in the second culture plate, with some monoclonal antibody remaining in excess.

Both culture plates were left overnight at 4° C. Then the first culture plate was washed three times with Tris/NaCl solution containing 0.05% Tween 20, leaving thrombospondin that had been present in the releasate adhered to the surfaces of the wells of the culture plate to make charged substrate units. Next, 175 μl portions of the contents of each well of the second plate were placed in the corresponding wells of the first, releasate-coated plate. After incubation at 24° C. for 30 minutes, this material was removed from the wells of the first culture plate, leaving any monoclonal antibody that had not been bound to thrombospondin contained in the dilutions bound to the thrombospondin adsorbed on the surfaces of the wells. The first culture plate was then washed three times in Tris/NaCl solution containing 0.05% Tween 20 to remove monoclonal antibody not attached to the wells.

A marker solution was then prepared of alkaline phosphatase-conjugated goat anti-mouse IgG (obtained from Kirkegaard and Perry, Gaithersburg, Md.) in a gelatin-containing buffer including Tris/NaCl solution containing 0.25% gelatin, 0.05% Nonidet P-40, 20 mM $ZnCl_2$, 1 mM $MgCl_2$, and 10% fetal calf serum. The marker solution was prepared so as to contain a 2 μg/ml concentration of the goat anti-mouse antibody. 200 μl of the marker solution was added to each of the 96 wells of the first culture plate to allow goat anti-mouse antibody to bind to any monoclonal antibody remaining in the wells. After incubation for two hours at 24° C., the first culture plate was washed three times with the gelatin-containing buffer. Then 200 μl of a solution containing 1 mg/ml of sodium p-nitrophenyl phosphate in Tris/NaCl, pH 9.0 was added to each well. The sodium p-nitrophenyl phosphate reacted with any phosphatase-conjugated goat anti-mouse antibody remaining in the wells to produce p-nitrophenyl. Thus, the appearance of p-nitrophenyl in a particular well indicated the presence of alkaline phosphate-conjugated goat anti-mouse IgG bound to monoclonal antibody bound in turn to thrombospondin adsorbed on the first culture plate. The p-nitrophenyl was quantitatively measured by monitoring 405 nm wavelength light transmitted therethrough with a conventional micro ELISA plate reader obtained from Dynatech, Alexandria, Va. Concentrations of thrombospondin in the test material were calculated by comparison with the known concentrations of thrombospondin in the dilutions of the thrombospondin standard.

ELISAs of Thrombospondin in Other Fluids: Quantitative competitive ELISAs of thrombospondin in accord with the example have been carried out successfully on normal human and canine plasma and on pathologic human plasma from patients having disseminated intervascular coagulation associated with septocemia, thrombotic thrombocytopemia purpura, cancers, and neoplasms. In addition, ELISAs for thrombospondin were performed on human joint fluids from people with various types of arthritic conditions and other joint disorders as well as on fetal calf serum, fluids derived from lysed human blood platelets, releasate from thrombin-stimulated blood platelets, and trypsinized, purified human thrombospondin.

EXAMPLE 3

Immunohistological Techniques

Confluent cell layers of human foreskin fibroblasts and, separately, human fetal lung fibroblasts were grown on glass coverslips. The cell layers were washed with Hanks' balanced salt solution (hereinafter HBSS). Then they were fixed with a 3.5% aqueous solution of formaldehyde by exposing the cell to the solution for 20 minutes at 20° C. The cells were then washed with HBSS and incubated with the monoclonal anti-thrombospondin antibody disclosed above for one hour at 20° C. The monoclonal antibody was prepared from mouse ascites fluid as disclosed above and used at a concentration of 4.8 µg/ml. Thereafter the cells were again washed with HBSS. Then the cells were stained by exposure for one hour at 20° C. to a 1:100 dilution of fluorescein-conjugated rabbit anti-mouse IgG (provided by Cappel Laboratories, Cochranville, Pa.). The cells were again washed with HBSS and then mounted on glass slides in a solution containing by volume 50% glycerol and 50% phosphate-buffered normal saline. Control experiments were done first by absorbing the monoclonal anti-thrombospondin antibody with a solution of purified thrombospondin having a concentration of 50 µg/ml. The purified thrombospondin was prepared in accord with the method disclosed above for preparing the innoculum antigen used in the production of monoclonal antibody to thrombospondin. Fluorescence observed with the monoclonal antibody was blocked only by absorption with thrombospondin.

EXAMPLE 4

Immunoisolation of Thrombospondin

Staphylococcal protein A-Sepharose 4B beads were incubated with rabbit anti-mouse IgG antibody. Excess rabbit anti-mouse antibody was removed by washing. Then the monoclonal antibody specified above was incubated with the beads, being bound thereto by the rabbit anti-mouse antibody. A mixed micelar solution containing thrombospondin was prepared from endothelial cell medium by methods set forth in Mosher, Doyle, & Jaffe, "Synthesis and Secretion of Thrombospondin by Cultured Human Endothelial Cells," *J. Cell Biol.* 93, 343–348 at 344 (1982). A sample of the solution was incubated with the beads bearing the monoclonal antibody. After overnight incubation with end-over-end rotation at 20° C., the beads were centrifuged and washed eight times with 2M urea, 0.1 M glycine 1% Triton X-100. Thrombospondin retained on the beads by coupling with the monoclonal antibody was eluted by boiling in 2% SDS, 2M urea. Successful isolation of thrombospondin by this means was confirmed by analysis of the material so isolated by polyacrylamide gel electrophoresis. Anti-ovalbumin was used as a control. The anti-ovalbumin and the rabbit anti-mouse IgG were both obtained from Cappel Laboratories, Cochranville, Pa.

From the examples disclosed, one skilled in the art will appreciate that the monoclonal antibody disclosed above may be utilized in a variety of ways with respect to the antigens for which it has been shown to be specific. Thus, it may be used to assay for thrombospondin in other ELISAs than competitive ELISAs of the sort disclosed, to locate thrombospondin in tissue sections by immunofluorscence, and to recognize electrophoretically separated thrombospondin or thrombospondin otherwise isolated after transfer onto nitrocellulose paper by conventional immunoblotting techniques. It may be used as well in other conventional methods for utilizing an antibody for assay and other purposes, whether by utilization of immunofluorscence, immunoperoxidase reactions, or other such techniques. When radiolabeled, the antibody may be used to localize thrombospondin in vivo by nuclear scanning, following conventional techniques. Thus, it is understood that the present invention is not limited to the particular reagents, steps, or methods disclosed herein. Instead, it embraces all such modified forms thereof as come within the scope of the following claims.

What is claimed is:

1. The hybridoma ATCC HB8432.

2. The monoclonal antibody prepared from the hybridoma of claim 1.

3. A method of assaying for the presence of thrombospondin in a sample of test material, comprising the steps of:

(a) binding known thrombospondin to adsorptor substrate units to produce thrombospondin charged substrate units;

(b) exposing a known quantity of the test material to a known quantity of the monoclonal antibody produced by hybridoma ATCC HB8432 so as to cause the monoclonal antibody to bind to any thrombospondin present in the test material to produce a reacted unknown sample;

(c) exposing a selected quantity of a standard preparation of thrombospondin having a known amount of thrombospondin to a known quantity of the monoclonal antibody so as to cause the monoclonal antibody to bind to the thrombospondin to create a reacted standard sample;

(d) exposing the reacted unknown sample to a first thrombospondin charged substrate unit to quantitatively react any yet unreacted monoclonal antibody contained in the reacted unknown sample with the bound thrombospondin thereon;

(e) exposing the reacted standard sample to a second thrombospondin charged substrate unit to quantitatively react any yet unreacted monoclonal antibody contained in the reacted standard sample with the bound thrombospondin thereon;

(f) removing monoclonal antibody not reacted with the bound thrombospondin on the thrombospondin charged substrate units; and (g) comparatively and quantitatively assaying for the presence of reacted monoclonal antibody on the first and second thrombospondin charged substrate units.

4. The method of claim 3 wherein the step of assaying for the presence of reacted monoclonal antibody on the first and second thrombospondin charged substrate units includes:

(a) exposing each thrombospondin charged substrate unit and monoclonal antibody reacted therewith to a marker-coupled anti-mouse antibody to allow the marker-coupled antibody to bind to any monoclonal antibody reacted with the thrombospondin on the thrombospondin charged substrate unit;

(b) removing the unbound portion of the marker-coupled antibody; and (c) measuring the amount of marker remaining on the thrombospondin charged substrate unit.

5. The method of claim 4 wherein the marker is an enzyme.

6. The method of claim 4 wherein the marker is a fluorescent material.

7. The method of claim 4 wherein the marker is a radioactive material.

8. The method of assaying for the presence of thrombospondin in a sample of test material, comprising the steps of:

(a) binding the test material to an adsorptor substrate;

(b) exposing the test material to monoclonal antibody produced by the hybridoma ATCC HB8432 to allow the antibody to bind to any thrombospondin present in the test material;

(c) removing the unbound portion of the monoclonal antibody; and (d) assaying for the presence of bound monoclonal antibody.

9. The method of claim 8 wherein the step of assaying for the presence of bound monoclonal antibody includes:

(a) exposing the test material and bound monoclonal antibody to a marker-coupled anti-mouse antibody to allow the marker-coupled antibody to bind to any monoclonal antibody bound to the test material;

(b) removing the unbound portion of the marker-coupled antibody; and (c) measuring the amount of marker remaining on the test material.

10. The method of claim 9 wherein the marker is an enzyme.

11. The method of claim 9 wherein the marker is a fluorescent material.

12. The method of claim 9 wherein the marker is a radioactive material.

13. The method of claim 9 wherein a known dilution of test material is used and wherein the step of assaying for the presence of bound monoclonal antibody includes measuring the amount of a marker quantitatively associated with the antibody by means of a reaction that may be quantitatively measured and that can be compared with the comparable reactions of known amounts of thrombospondin bound to the monoclonal antibody, whereby the assay for the presence of thrombospondin may be a quantitative assay.

14. A method of microscopically examining a substantially cohesive non-fluid test material for the presence of thrombospondin, comprising the steps of:

(a) incubating the test material with the monoclonal antibody produced by the hybridoma ATCC HB8432 to bind the monoclonal antibody to thrombospondin present in the test material;

(b) removing the unbound portion of the monoclonal antibody;

(c) incubating the test material with a marker-labeled anti-mouse antibody to bind the marker-labeled antibody to the monoclonal antibody that is bound to thrombospondin in the test material; and (d) microscopically observing the test material under conditions adapted to render the marker visually perceivable.

15. The method of claim 4 wherein the marker is an enzyme.

16. The method of claim 14 wherein the marker is a fluorescent material.

* * * * *

UNITED STATES PATENT OFFICE
CERTIFICATE OF CORRECTION

Patent No. 4,610,960          Dated Sep. 9, 1986

Inventor(s) Deane F. Mosher

It is certified that error appears in the above-identified patent and that said Letters Patent are hereby corrected as shown below:

In Column 2, line 37, change "body'esponse" to -- body's response --.

In Column 12, line 40, change "claim 4" to -- claim 14 --.

Signed and Sealed this

Sixth Day of January, 1987

Attest:

DONALD J. QUIGG

Attesting Officer          Commissioner of Patents and Trademarks